US010517883B2

(12) United States Patent
Danenberg et al.

(10) Patent No.: US 10,517,883 B2
(45) Date of Patent: *Dec. 31, 2019

(54) METHOD OF TREATING ACUTE MYOCARDIAL INFARCTION

(75) Inventors: Haim D. Danenberg, Mevaseret Zion (IL); Gershon Golomb, Efrat (IL); Elazer R. Edelman, Brookline, MA (US)

(73) Assignee: ZULI HOLDINGS LTD., Tel Aviv (IL)

( * ) Notice: Subject to any disclaimer, the term of this patent is extended or adjusted under 35 U.S.C. 154(b) by 1061 days.

This patent is subject to a terminal disclaimer.

(21) Appl. No.: 10/607,623

(22) Filed: Jun. 27, 2003

(65) Prior Publication Data

US 2004/0265391 A1  Dec. 30, 2004

(51) Int. Cl.
| | |
|---|---|
| *A61K 31/663* | (2006.01) |
| *A61K 9/127* | (2006.01) |
| *A61K 9/51* | (2006.01) |
| *A61K 31/66* | (2006.01) |
| *A61K 31/675* | (2006.01) |

(52) U.S. Cl.
CPC .......... *A61K 31/663* (2013.01); *A61K 9/127* (2013.01); *A61K 9/51* (2013.01); *A61K 31/66* (2013.01); *A61K 31/675* (2013.01)

(58) Field of Classification Search
USPC .............................. 424/489; 514/102, 964, 89
See application file for complete search history.

(56) References Cited

U.S. PATENT DOCUMENTS

| | | | |
|---|---|---|---|
| 4,067,971 A | 1/1978 | Francis et al. | |
| 4,216,211 A | 8/1980 | Francis | |
| 4,990,503 A * | 2/1991 | Isomura et al. | ........... 514/80 |
| 4,997,454 A | 3/1991 | Violante et al. | |
| 5,096,717 A | 3/1992 | Wirth et al. | |
| 5,196,409 A | 3/1993 | Breuer et al. | |
| 5,312,954 A | 5/1994 | Breuer et al. | |
| 5,338,731 A | 8/1994 | Breuer et al. | |
| 5,356,887 A | 10/1994 | Brener et al. | |
| 5,492,926 A | 2/1996 | Cullinan et al. | |
| 5,527,538 A | 6/1996 | Baldeschwieler | |
| 5,652,227 A | 7/1997 | Teronen et al. | |
| 5,698,531 A * | 12/1997 | Nabel | ........... A61B 17/22 435/320.1 |
| 5,733,564 A | 3/1998 | Lehtinen | |
| 5,741,514 A | 4/1998 | Barenholz et al. | |
| 5,746,223 A | 5/1998 | Williams | |
| 5,760,030 A | 6/1998 | Bryant et al. | |
| 5,776,429 A | 7/1998 | Unger et al. | |
| 5,792,885 A | 8/1998 | Ham et al. | |
| 5,811,118 A | 9/1998 | Ostro et al. | |
| 5,820,879 A | 10/1998 | Fernandez et al. | |
| 5,882,656 A | 3/1999 | Bechard et al. | |
| 5,932,563 A | 8/1999 | Stokes et al. | |
| 5,932,580 A | 8/1999 | Levitzki et al. | |
| 5,994,341 A | 11/1999 | Hunter et al. | |
| 6,030,639 A | 2/2000 | Janoff et al. | |
| 6,090,777 A * | 7/2000 | Hack et al. | ........... 514/2 |
| 6,121,278 A | 9/2000 | Jackson et al. | |
| 6,139,871 A | 10/2000 | Hope | |
| 6,245,757 B1 | 6/2001 | Chopp et al. | |
| 6,306,421 B1 | 10/2001 | Kunz et al. | |
| 6,432,413 B1 | 8/2002 | Loeb | |
| 6,719,998 B1 * | 4/2004 | Golomb et al. | ........... 424/450 |

(Continued)

FOREIGN PATENT DOCUMENTS

| | | |
|---|---|---|
| DE | 196 37 890 A1 | 3/1998 |
| EP | 0339237 | 11/1989 |

(Continued)

OTHER PUBLICATIONS

Pennanen et al., Effect of Liposomal and Free Bisphosphonates on the IL-1β, IL-6 and TNF-α Secretion from RAW 264 Cells in Vitro, Pharmaceutical Research, vol. 12 No. 6 1995 pp. 916-922.*
Maximilian et al., Effect of EHDP on Calcium Accumulation and Technetium-99m Pyrophosphate Uptake in Experimental Myocardial Infarction, 1981, Circulation, vol. 64, No. 5, pp. 1012-1017.*
Mateos-Cáreres et al., Prior aspirin use in unstable angina patients with modified plasma inflammatory markers and endothelial nitric oxide synthase in neutrophils, 2002, European Journal of Clinical Investigation, vol. 32, pp. 895-900.*
Taubes et al., Does Inflammation Cut to the Heart of the Matter?, 2002, Science, vol. 296, No. 5566, pp. 242-245.*

(Continued)

*Primary Examiner* — Jeffrey S Lundgren
*Assistant Examiner* — Michael J Schmitt
(74) *Attorney, Agent, or Firm* — Cadwalader, Wickersham & Taft LLP (57) ABSTRACT

A method of treating an acute myocardial infarction by administering to an individual an effective amount of a formulation which inhibits and/or depletes phagocytic cells with high specificity, thereby suppressing the inflammatory response that occurs during and following acute myocardial infarction. The formulation comprises an agent which is an intra-cellular inhibitor that is released within the targeted phagocytic cells, specifically macrophage/monocytes, and inhibits and/or destroys the macrophages and/or monocytes, thereby reducing the final zone of infarct and improving cardiac repair and myocardial remodeling. Since macrophages and monocytes possess the unique ability to phagocytose large bodies, the agent is formulated into a specific size such that it can enter cells primarily via phagocytosis. Thus, the specifically sized formulation selectively targets monocytes/macrophages. The formulation may comprise an encapsulated agent, an embedded agent or a particulate agent, wherein the formulation is of a specific size, such that it can enter cells primarily via phagocytosis. The formulation is preferably in the size range of 0.03-1.0 microns.

11 Claims, 3 Drawing Sheets

(56) References Cited

U.S. PATENT DOCUMENTS

| | | | |
|---|---|---|---|
| 6,770,466 | B2 | 8/2004 | Shi et al. |
| 6,984,400 | B2* | 1/2006 | Golomb et al. ............... 424/489 |
| 7,008,645 | B2* | 3/2006 | Golomb et al. ............... 424/489 |
| 9,498,488 | B2 | 11/2016 | Richter et al. |
| 2001/0031741 | A1 | 10/2001 | Ziegler et al. |
| 2002/0025313 | A1 | 2/2002 | Micklus et al. |
| 2002/0110588 | A1 | 8/2002 | Hope et al. |
| 2002/0160495 | A1* | 10/2002 | Mirochnitchenko et al. ............... 435/226 |
| 2002/0187184 | A1 | 12/2002 | Golomb et al. |
| 2002/0192157 | A1 | 12/2002 | Low et al. |
| 2003/0013686 | A1* | 1/2003 | Golomb et al. ............... 514/102 |
| 2003/0091547 | A1 | 5/2003 | Edelberg et al. |
| 2003/0100514 | A1 | 5/2003 | Ahotupa et al. |
| 2004/0265391 | A1 | 12/2004 | Danenberg et al. |

FOREIGN PATENT DOCUMENTS

| | | |
|---|---|---|
| EP | 0459318 | 12/1991 |
| WO | WO 88/00289 | 1/1988 |
| WO | WO 93/09790 | 5/1993 |
| WO | WO 96/20698 | 7/1996 |
| WO | WO 97/16170 | 5/1997 |
| WO | WO 97/33552 | 9/1997 |
| WO | WO 97/43437 | 11/1997 |
| WO | WO 98/31359 | 7/1998 |
| WO | WO 99/17740 | 4/1999 |
| WO | WO 99/38998 | 8/1999 |
| WO | WO 00/03677 | 1/2000 |
| WO | WO 00/21540 | 4/2000 |
| WO | WO 00/34293 | 6/2000 |
| WO | WO 00/56806 | 9/2000 |
| WO | WO 00/64516 | 11/2000 |
| WO | WO 00/69412 | 11/2000 |
| WO | WO 00/69503 | 11/2000 |
| WO | WO 01/74337 | 10/2001 |
| WO | WO 02/083096 | 10/2002 |
| WO | WO 03/020243 A1 | 3/2003 |
| WO | WO 03/086351 | 10/2003 |
| WO | WO 03/089568 | 10/2003 |
| WO | WO 03/097696 | 11/2003 |
| WO | WO 2005/002545 | 1/2005 |
| WO | WO 2005/044175 | 5/2005 |

OTHER PUBLICATIONS

Li et al., Kinetics of tumor necrosis factor α in plasma and the cardioprotective effect of a monoclonal antibody to tumor necrosis factor α in acute myocardial infarction, 1999, American Heart Journal, vol. 137, No. 6, pp. 1145-1152.*
Cipollone et al., "Elevated Circulating Levels of Monocyte Chemoattractant Protein-1 in Patients with Restenosis After Coronary Angioplasty", 2001, Arterioscler Thromb Vasc Biol, vol. 21, pp. 327-334.*
Maekawa et al. Prognostic Significance of Peripheral Monocytosis: After Reperfused Acute Myocardial Infarction: A Possible Role for Left Ventricular Remodeling, 2002, J Am Coll Cardiol, vol. 39, No. 2, pp. 241-246.*
Corsini et al., Cloricromene, as semi-synthetic coumarin derivative, inhibits tumor necrosis factor-α production at a pre-transcriptional level, 2001, European Journal of Pharmacology, vol. 418, pp. 231-237.*
D'Souza et al., Macrophage Depletion by Albumin Microencapsulated Clodronate: Attenuation of Cytokine Release in Macrophage-dependent Glomerulonephritis, 1999, Drug Development and Industrial Pharmacy, vol. 25 (5), pp. 591-596.*
Mönkkönen and Heath, 1993, "The effects of liposome-encapsulated and free clodronate on the growth of macrophage-like cells in vitro: the role of calcium and iron" Calcif. Tissue Int. 53:139-146.
Mönkkönen et al., 1995, "Studies on liposome formulations for intra-articular delivery of clodronate" J. Controlled Release 35:145-154.
Patashnik et al., 1997, "Preparation and evaluation of chitosan microspheres containing bisphosphonates" J. Drug Targeting 4:371-380.
Ylitalo, 2002, "Bisphosphonates and atherosclerosis" General Pharmacology 35:287-296.
Tashiro et al., 1995, "Monocyte-related cytokines in acute myocardial infarction" American Heart Journal 130:446-452.
Ylitalo, et al., "Effects of Liposome-Encapsulated Bisphosphonates on Acetylated LDL Metabolism. Lipid Accumulation and Viability of Phagocyting Cells," Life Sciences, Vo. 62. No. 5. pp. 413-422, (2002).
European Patent Office, Communication Pursuant to Article 94(3) EPC, App. No. 04785964.0, dated Jan. 22, 2008.
Beers and Berkow, The Merck Manual of Diagnosis and Therapy, Merck Research Laboratories, Whitehouse Station, 1999.
European Patent Office, Communication pursuant to Article 94 (3) EPC, App. No. 04756133.7, dated Jan. 22, 2008.
Hyvonen, et al., "Influence of dichloromethylene bisphosphonate on the in vitro phagocytosis of hydroxyapatite particles by rat peritoneal exudate cells: an electron microscopic and chemiluminescence study," Ann. Rheum. Dis., vol. 51: 203-209 (1992).
Flora, "Comparative Antiinflammatory and Bone Protective Effects of Two Diphosphonates in Adjuvant Arthritis," Arthritis Rheum., vol. 22(4): 340-346 (1979).
Van Offel, et al., "Influence of cyclic intravenous pamidronate on proinflammatory monocytic cytokine profiles and bone density in rheumatoid arthritis treated with low dose prednisolone and methotrexate," Clin. Exp. Rheum., vol. 19: 13-20 (2001).
Mullane, et al., "Role of Leukocytes in Acute Myocardial Infarction in Anesthetized Dogs: Relationship to Myocardial Salvage by Anti-inflammatory Drugs," J. Pharm. Exp. Ther., vol. 228(2): 510-522 (1984).
Siiteri, et al., "Immunologic and Endocrine Interrelationships in Pregnancy," Biol. Reprod., vol. 26: 1-14 (1982).
Schroeter, et al., "Phagocytic Response in Photochemically Induced Infarction of Rat Cerebral Cortex," Stroke, vol. 28: 382-386 (1997).
Witte, et al., "Delayed and Remote Effects of Focal Cortical Infarctions: Secondary Damage and Reactive Plasticity," Adv. Neurol., vol. 73: 207-227 (1997).
Martin, et al., "Bisphosphonates—mechanisms of action," Australian Prescriber, vol. 23, No. 6: 130-132 (2000).
Goldmann, et al., "Risk Stratification in Acute Coronary Syndrome," Herz, vol. 26, Supplement 1, pp. S24-S29, Background Section, Mar. 2001.
International Search Report and Written Opinion dated Dec. 23, 2005 for corresponding application PCT/US2004/020536.
International Search Report and Written Opinion dated Dec. 15, 2004 for related application PCT/US2004/020487.
International Search Report and Written Opinion dated Jul. 29, 2008 for related application PCT/IB06/02028.
Kramsch, et al., "The Effect of Agents Interfering with Soft Tissue Calcification and Cell Proliferation on Calcific Fibrous-Fatty Plaques in Rabbits," Circulation Res., 42(4):562-570 (1978).
Monkkonen, et al., "Growth Inhibitions of Macrophage-Like and Other Cell Types by Liposome-Encapsulated, Calcium-Bound, and Free Bisphosphonates In Vitro," J. Drug Targeting, 2:299-308 (1994).
Donbrow, "Microcapsules and Nanoparticles in Medicine and Pharmacy," CRC Press, Boca Raton, FL, pp. 1-347 (1992).
Paspaliaris, et al., "Clodronate Inhibits Contraction and Prevents the Action of L-Type Calcium Channel Antagonists in Vascular Smooth Muscle," J. Bone Min. Res., 6(8):835-841 (1991).
Van Rooijen, et al., "In vivo elimination of macrophages in spleen and liver, using liposome encapsulated drugs: methods and applications," Liposomes as drug carriers: Trends and progress, Ed. G. Gregoriadis, John Wiley and Sons, Chichester, U.K. (chapter 9), pp. 131-143 (1988).
Thepen, et al., "Alveolar macrophage elimination in vivo is associated with an increase in pulmonary immune response in mice," J. Exp. Med., 170:499-509 (1989).
Monkkonen, et al., "Effects of clodronate and pamidronate on splenic and hepatic phagocytic cells of mice," Pharmacol. Toxicol., 68:284-286 (1991).

(56) References Cited

OTHER PUBLICATIONS

Van Rooijen, N., "Liposomes as an in vivo tool to study and manipulate macrophage function: Introduction 41$^{st}$ Forum in Immunology," *Res. Immunol.*, 143:177-178 (1992).
Biewenga, et al., "Macrophage depletion in the rat after intraperitoneal administration of liposome-encapsulated clodronate: depletion kinetics and accelerated repopulation of peritoneal and omental macrophage by administration of Freund's adjuvant," *Cell. Tissue Res.*, 280:189-196 (1995).
Gaytan, et al., "In vivo manipulation (depletion versus activation) of testicular macrophages: central and local effects," *J. Endocrinol.*, 150:57-65 (1996).
Van Rooijen, et al., "Transient suppression of macrophage functions by liposome-encapsulated drugs," *Trends in Biotechnology*, 15(5):178-185 (1997).
Van Rooijen, et al., "Macrophage subset repopulation in the spleen: differential kinetics after liposome-mediated elimination," *J. Leuk. Biol.*, 45:97-104 (1989).
Van Rooijen, N., "Macrophages as accessory cells in the in vivo humoral immune response: from processing of particulate antigens to regulation by suppression," *Semin. Immunol.*, 4:237-245 (1992).
www.clodronateliposomes.com, copyright (c) 1984-2003, download date Sep. 4, 2003.
Van Rooijen, et al., "In vitro and in vivo elimination of macrophage tumor cells using liposome-encapsulated dichloromethylene diphosphonate," *Virchows Arch. B (Cell Pathol.)*, 54:241-245 (1988).
Van Rooijen, et al., "Liposome mediated depletion of macrophages: mechanism of action, preparation of liposomes and applications," *J. Immunol. Methods*, 174:83-93 (1994).
Langer, R., "New Methods of Drug Delivery," *Science*, 249:1527-33 (1990).
Cohen, et al., "Synthesis and Preclinical Pharmacology of 2-(2-Aminopyrimidinio) Ethylidene-1,1-Bisphosphonic Acid Betaine (ISA-13-1)—A Novel Bisphosphonate," *Pharma. Res.*, 16(9):1399-1406 (1999).
Interview Summary dated Nov. 17, 2009 in prosecution of related U.S. Appl. No. 11/190,787.
Buiting, et al., "Liposomes as antigen carriers and adjuvants in vivo," *Res. Immunol.*, 143:541-548 (1992).
Bergh, et al., "Liposome-mediated macrophage depletion: an experimental approach to study the role of testicular macrophage in the rat," *J. Endocrinology*, 136:407-413 (1993).
Van Rooijen, et al., "Apoptosis of macrophages induced by liposome-mediated intracellular delivery of clodronate and propamidine," *J. Immunol. Methods*, 193:93-99 (1996).
Leenars, et al., "Increased adjuvant efficacy in stimulation of antibody responses after macrophage elimination in vivo," *Immunol*, 90:337-343 (1997).
European Search Report and Written Opinion for related EP application 06795155.8-2112 dated Sep. 14, 2009.
Luckman, et al., "Nitrogen-Containing Bisphosphonates Inhibit the Mevalonate Pathway and Prevent Post-Tranlational Prenylation of GTP-Binding Proteins, Including Ras," *J. Bone Min. Res.*, 13:581-589 (1998).
Non-Final Office Action dated Nov. 26, 2007 in prosecution of related U.S. Appl. No. 10/871,488.
Applicants' response to Nov. 26, 2007 Non-Final Office Action filed Feb. 25, 2008 in prosecution of related U.S. Appl. No. 10/871,488.
Non-Final Office Action dated May 21, 2008 in prosecution of related U.S. Appl. No. 10/871,488.
Examiner Interview Summary dated Jul. 3, 2008 in prosecution of related U.S. Appl. No. 10/871,488.
Presentation by Inventor Yoram Richter from Examiner Interview submitted Aug. 21, 2008 in prosecution of related U.S. Appl. No. 10/871,488.
Rule 132 Declaration by Inventor Yoram Richter submitted Aug. 21, 2008 in prosecution of related U.S. Appl. No. 10/871,488.
Applicants' response to May 21, 2008 Non-Final Office Action filed Aug. 21, 2008 in prosecution of related U.S. Appl. No. 10/871,488.
Non-Final Office Action dated Sep. 25, 2008 in prosecution of related U.S. Appl. No. 10/871,488.
Applicants' response to Sep. 25, 2008 Non-Final Office Action filed Jan. 26, 2006 in prosecution of related U.S. Appl. No. 10/871,488.
Applicants' supplemental response to Sep. 25, 2008 Non-Final Office Action filed Jan. 26, 2009 in prosecution of related U.S. Appl. No. 10/871,488.
Boras, et al., "Diabetes and Coronary Heart Disease," *Endocrinology and Metabolic Diseases*, 31-4:199-208 (2002).
"Unnerving Truth About Diabetic Neuropahty," Diabetic Facts, Diabetes Research, http://www.allaboutdiabetes.net/unnerving-truth-diabetic-neuropathy . . . .
Non-Final Office Action dated Apr. 16, 2009 in prosecution of related U.S. Appl. No. 10/871,488.
Applicants' response to Apr. 16, 2009 Non-Final Office Action filed Jul. 13, 2009 in prosecution of related U.S. Appl. No. 10/871,488.
Final Office Action dated Oct. 29, 2009 in prosecution of related U.S. Appl. No. 10/871,488.
Restriction Requirement dated Jul. 29, 2008 in prosecution of related U.S. Appl. No. 11/190,787.
Applicants' response to Jul. 29, 2008 Restriction Requirement filed Aug. 29, 2008 in prosecution of related U.S. Appl. No. 11/190,787.
Non-Final Office Action dated Oct. 29, 2008 in prosecution of related U.S. Appl. No. 11/190,787.
Applicants' response to Oct. 29, 2008 Non-Final Office Action filed Feb. 25, 2009 in prosecution of related U.S. Appl. No. 11/190,787.
Non-Final Office Action dated Jun. 11, 2009 in prosecution of related U.S. Appl. No. 11/190,787.
Applicants' response to Jun. 11, 2009 Non-Final Office Action filed Nov. 10, 2009 in prosecution of related U.S. Appl. No. 11/190,787.
Applicants' supplemental response to Jun. 11, 2009 Non-Final Office Action filed Nov. 10, 2009 in prosecution of related U.S. Appl. No. 11/190,787.
Remington's Pharmaceutical Sciences, A.R. Gennaro, ed., Mack Publishing Co. (18$^{th}$ ed. 1990), p. 993.
Cendejas-Santana, et al., "Progesterone crystallization from a solvent: a new procedure," *Mat. Res. Innovat.*, 6:252-255 (2002).
Afergan, et al., "Delivery of serotonin to the brain by monocytes following phagocytosis of liposomes," *J. Controlled Rel.*, 132:84-90 (2008).
Monkkonen, et al., "The effects of liposome surface charge and size on the intracellular delivery of clodronate and gallium in vitro," *Int. J. Pharm.*, 107:189-197 (1994).
Selander, et al., "Characteristics of the Clodronate-Induced Apoptosis in Osteoclasts and Macrophages," *Mol. Pharmacol.*, 50:1127-1138 (1996).
Benford, et al., "Farnesol and Geranylgeramiol Prevent Activation of Caspases by Aminobisphosphonates: Biochemical Evidence for Two Distinct Pharmacological Classes of Bisphosphonate Drugs," *Mol. Pharmacol.*, 56:131-140 (1999).
Frith, et al., "The Molecular Mechanism of Action of the Antiresorptive and Antiinflammatory Drug Clodronate: Evidence for the Formation In Vivo of a Metabolite That Inhibits Bone Resorption and Causes Osteoclast and Macrophage Apoptosis," *Arth. Rheum.*, 44:2201-2210 (2001).
Monkkonen, et al., "The Cellular Uptake and Metabolism of Clodronate in RAW 264 Macrophages," *Pharm. Res.*, 18:1550-1555 (2001).
Lehenkari, et al., "Further Insight into Mechanism of Action Clodronate; Inhibition of Mitochondrial ADP/ATP Translocase by a Nonhydrolyzable, Adenine-Containing Metabolite," *Mol. Pharmacol.*, 62:1253-1262 (2002).
Makkonen, et al., "Different Effects of Three Bisphosphonates on Nitric Oxide Production by Raw 264 Macrophage-Like Cells in Vitro," *J. Pharmacol. Exp. Ther.*, 277:1097-1102 (1996).
Monkkonen, et al., "Effects of Tiludronate and Ibandronate on the Secretion of Proinflammatory Cytokines and Nitric Oxide from Macrophages In Vitro," *Life Sci.*, 62:PL95-102 (1998).
Makkonen, et al., "Contrasting effects of alendronate and clodronate on RAW 264 macrophages: the role of a bisphosphonate metabolite," *Eur. J. Pharm. Sci.*, 8:109-118 (1999).

(56) References Cited

OTHER PUBLICATIONS

Toyras, et al., "Inhibition of mevalonate pathway is involed in alendronate-induced cell growth inhibition, but not in cytokine secretion from macrophages in vitro," *Eur. J. Pharm. Sci.*, 19:223-230 (2003).

Monkkonen, et al., "Liposome-Mediated Delivery of Gallium to Macrophage-Like Cells in Vitro: Demonstration of a Transferrin-Independent Route for Intracellular Delivery of Metal Ions," *Pharm. Res.*, 10(8):1130-1135 (1993).

Van Lent, et al., "In Vivo Role of Phagocytic Synovial Lining Cells in Onset of Experimental Arthritis," *Am. J. Pathol.*, 143:1226-37 (1993).

Rogers, et al., "Monocyte Recruitment and Neointimal Hyperplasia in Rabbits," *Arteriosclerosis, Thrombosis, and Vascular Biology*, 16:1312-18 (1996).

Kumitomo, et al., Abstract, "Experimental Induction of Athero Sclerosis in Guinea-Pigs Fed a Cholesterol Vitamin D-2-Rich Diet" (1983).

Fleisch, "Bisphosphonates in bone disease," Parthenon Publishing Group Inc., pp. 184-210 (1997).

Mak, et al., "Clinical Trials to prevent Restenosis adter Percutaneous Coronary Revascularization," *The NY Academy of Sciences*, pp. 225-277 (1994).

Leclerc, et al., "Drug prevention of restenosis after angioplasty: an update," Elsevier Science, pp. 722-724 (1995).

Lefkovits, et al., "Pharmacological Approaches for the Prevention of Restenosis After Percutaneous Corornary Intervention," *Progress in Cardiovascular Disease*, 40(2):141-58 (1997).

Hamon, et al., "Restenosis after coronary angioplasty," *Eur. Heart J.*, 16:33-48 (1995).

Gottsauner-Wolf, et al., "Influence of local delivery of the protein tyrosine kinase receptor inhibitor tyrphostin-47 on smooth-muscle cell proliferation in a rat carotid balloon-injury model," *Am. Heart J.*, 19:347-56 (1996).

Shioi, et al., "β-Glycerophosphate Accelerates Calcification in Cultured Bovine Vascular Smooth Muscle Cells," *Arteriosclerosis, Thrombosis and Vascular Biology*, 15(11):2003-9 (1995).

Bellah, et al., "Idiopathic arterial calcification of infancy: Prenatal and postnatal effects of therapy in an infant," *The Journal of Pediatrics*, 121(6):930-3 (1992).

Waller, et al., "Coronary Artery and Saphenous Vein Graft Remodeling: A Review of Histologic Findings after Various Interventional Procedure—Part VI," *Clin. Cardiol.*, 20:153-60 (1997).

Anderson, et al., "A review of randomized trials comparing coronary angioplasty and bypass grafting," *Curr-Opin-Cardiol.*, 11(6):583-90 (1996).

Moorman, et al., "Percutaneous Transluminal Coronary Angioplasty (PTCA): Long-term Outcome and Aeromedical Implications," *Aviation, Space and Environmential Medicine*, 67(10):990-6 (1996).

Laurent, et al., "The arterial wall: a new pharmacological and therapeutic target," *Fundam. Clin. Pharmacol.*, 10:243-57 (1996).

Schwartz, "The vessel wall reaction in restenosis," *Semin. Intervent. Cardiol.*, 2:83-8 (1997).

Allaire, et al., "Endothelial Cell Injury in Cardiovascular Surgery: The Intimal Hyperplastic Response," *Ann. Thorac. Surg.*, 63(2):582-91 (1997).

Webb, et al., "Inhibition of Bioprosthetic Heart Valve Calcification with Aminodiphosphonate Covalently Bound to Residual Aldehyde Groups," *Ann. Thorac. Surg.*, 46:309-16 (1988).

Wagner, et al., "Contrasting Effects of Ethane-1-Hydroxy-1, 1-Diphosphonate (EHDP) on the Regression of two types of Dietary-Induced Atherosclerosis," *Atherosclerosis*, 27:419-35 (1977).

Daoud, et al., "The effect of ethane-1-hydroxy-1, 1-diphosphonate (EHDP) on necrosis of atherosclerotic lesion," *Atherosclerosis*, 67:41-8 (1987).

Walsh, et al., "Molecular strategies to inhibit restenosis: modulation of the vascular myocyte phenotype," *Semin. Intervent. Cardiol.*, 1:173-9 (1996).

Herrman, et al., "Pharmacological Approaches to the Prevention of Restenosis Following Angioplasty," *Drugs*, 46(1):15-52 (1993).

Rubin, et al., "Cellular and Molecular Mechanisms of Radiation Inhibition of Restenosis. Part 1: Role of the Macrophage and Platelet-Derived Growth Factor," *Int. J. Radiation Oncology Biol. Phys.*, 40:929-41 (1998).

Makkar, et al., "Prevention of Restenosis by Local Drug Delivery," *J. Cardiovasc. Pharmacol. Therapeut.*, 1(2):177-88 (1996).

Arefieva, et al., "Monocyte Integrin Expression and Monocyte-Platelet Complex Formation in Humans with Coronary Restenosism," *Clin. Exp. Pharm. Physio.*, 28:804-8 (2001).

Bohm, et al., "Exogenous Hepatitis B Surface Antigen Particles Processed by Dendritic Cells or Macrophages Prime Murine MHC Class I-Restricted Cytotoxic T Lymphocytes In Vivo," *J. Immunol.*, 155:3313-21 (1995).

Buiting, et al., "Liposomes as antigen carriers and adjuvants in vivo," *Res. Immunol.*, 143:541-8 (1992).

Bergh, et al., "Liposome-mediated marcophage depletion: an experimental approach to study the role of testicular macrophage in the rat," *J. Endocrinol.*, 136:407-13 (1993).

Van Rooijen, et al., "Apoptosis of macrophages induced by liposome-mediated intracellular delivery of clodronate and propamidine," *J. Immunol. Methods*, 193:93-9 (1996).

Leenars, et al., "Increased adjuvant efficacy in stimulation of antibody responses after macrophage elimination in vivo," *Immunol.*, 90:337-43 (1997).

Yue, et al., "In Vivo Myocardial Protection From Ischemia/Reperfusion Injury by the Peroxisome Proliferator-Activated Recepter-γ Agonist Rosiglitazone," *Circulation*, 104:2588-94 (2001).

Bolli, et al., "Evidence That Late Preconditioning Against Myocardial Stunning in Conscious Rabbits Is Triggered by the Generation of Nitric Oxide," *Circulation Res.*, 81:42-52 (1997).

Zhao, et al., "Myocardial apoptosis and ischemic preconditioning," *Cardiovasc. Res.*, 55:438-55 (2002).

Van Rooijen, et al., "The macrophage as target or obstacle in liposome-based targeting strategies," *Int. J. Pharmaceu.*, 162:45-50 (1998).

Matthews, et al., "Comparison of the response of primary human peripheral blood mononuclear phagocytes from different donors to challenge with model polyethylene particles of known size and dose," *Biomaterials*, 21:2033-44 (2000).

Fisher, et al., "Alendronate mechanism of action: geranylgeraniol, an intermediate in the mevalonate pathway, prevents inhibition of osteoclast formation, bone resorption, and kinase activation in vitro," *Cell Biol.*, 96:133-8 (1999).

Sansoni, et al., "Inhibition of antigen-presenting cell function by alendronate in vitro," *J. Bone Min. Res.*, 10(11):1719-25 (1995).

Lodge-Patch, "The Ageing of Cardiac Infarets, and its Influence on Cardiac Rupture," *Br. Heart J.*, pp. 37-42 (1951).

Jalowy, et al., "AT1 receptor blockade in experimental myocardial ischemia/reperfusion," *Basic Res. Cardiol.*, 93(2):85-91 (1998).

Response filed Dec. 22, 2009 in related U.S. Appl. No. 10/871,488 in response to Oct. 29, 2009 Final Office Action.

Non-Final Office Action is related U.S. Appl. No. 11/190,787 dated Mar. 3, 2010.

Response filed Jun. 1, 2010 in related U.S. Appl. No. 11/190,787 in response to Mar. 3, 2010 Non-Final Office Action.

Gennaro, "Parenteral Preparations," *Remington: The Science and Practice of Pharmacy*, 20th Ed., Ch. 41, pp. 780-920 (2000).

Makkonen, et al., "The effect of free gallium and gallium in liposomes on cytokine and nitric oxide secretion from macrophage-like cells in vitro," *Inflamm. Res.*, 44:523-528 (1995).

Van Rooijen et al., "Elimination of Phagocytic Cells in the Spleen after Intravenous Injection of Liposome-Encapsulated Dichloromethylene Diphosphonate: An Enzyme-Histochemical Study," Cell and Tissue Research (1984) 238: pp. 355-358.

YourDictionary, scientific definition of "heart attack", accessed Jun. 2, 2011 from http://science.yourdictionary.com/heart-attack.

Office Actions and Responses of related pending U.S. Appl. No. 10/871,488: Non-Final Rejection dated Mar. 4, 2011; and Response to Final Rejection with Request for Continued Examination dated Dec. 22, 2009.

Office Actions and Responses of related pending U.S. Appl. No. 11/190,787: Final Office Action dated Jun. 10, 2011.

(56) References Cited

OTHER PUBLICATIONS

Extended European Search Report and Opinion for EP 10010616.0-1219 (published as EP2266536) dated Sep. 17, 2012.
Office Actions and Responses of related U.S. Appl. No. 10/871,488: Amendment and Response to Final Rejection with RCE dated Feb. 9, 2012; Applicant Initiated Interview Summary dated Dec. 8, 2011; Final Rejection dated Nov. 10, 2011; and Amendment and Response to Non-Final Rejection with Extension of Time dated Aug. 24, 2011.
Office Actions and Responses of related U.S. Appl. No. 11/190,787: Notice of Abandonment dated May 31, 2012; Non-Final Rejection dated Nov. 17, 2011; and Amendment and Response to Final Rejection with RCE dated Sep. 9, 2011.
Definition of "opsonization" by the Free Dictionary, retrieved from http://www.thefreedictionary.com/opsonization on Nov. 28, 2014, pp. 1-2.
Aikawa, Masanori, "Vascular Biology of the Acute Coronary Syndromes," Cardiovascular Division. Department of Medicine, Brigham and Women's Hospital, Harvard Medical School, Experimental Medicine, vol. 20, No. 3, 2002, p. 434-442.
Saito et al., "An Investigation of the Stabilization and Regression of Coronary Lesions by Lipid-Lowering Therapy," 66$^{th}$ Annual Scientific Meeting of the Japanese Circulation Society Conference, Japanese Circulation Journal, vol. 10, No. 2, Oct. 2002, p. 233-236.
Office Actions of related U.S. Appl. No. 10/871,488: Non-Final Rejection dated Sep. 24, 2013.
Athlin et al., "Phagocytosis of Yeast Cells by Monocytes: Effects of Fluorouracil, Doxorubicin and Mitomycin," European Journal of Surgical Oncology, 1987, vol. 13, No. 1, pp. 51-55.
Bogdan et al., "Taxol, a Microtubule-Stabilizing Antineoplastic Agent, Induces Expression of Tumor Necrosis Factor α and Interleukin-1 in Macrophages," Journal of Leukocyte Biology, vol. 52, Jul. 1992, pp. 119-121.
Cooper et al., "Rapamycin But Not FK506 Inhibits the Proliferation of Mononuclear Phagocytes Induced by Colony-Stimulating Factors," Transplantation, vol. 57, No. 3, Feb. 1994, pp. 433-439.
Danenberg et al., "Macrophage Depletion by Clodronate-Containing Liposomes Reduces Neointimal Formation After Balloon Injury in Rats and Rabbits," Circulation: Journal of the American Heart Association, Jul. 15, 2002, pp. 599-605.
Iimuro et al., "Improvement of Survival Rate in Endotoxin Shock Model Rat by Administration of GdCl$_3$, Inhibitor of Liver Macrophage Phagocytosis," Digestive Organ and Immunology, No. 26, 1992, pp. 186-191.
Rosol et al., "Effects of Mithramycin on Calcium Metabolism and Bone in Dogs," Veterinary Pathology Online, vol. 29, pp. 223-229 (1992).
Suresh et al., "In Vitro Activation of Murine Bone Marrow-Derived Macrophages with Cisplatin and Mitomycin-C," Int. J. Immunopharmac., vol. 13, Nos. 2/3, pp. 189-195, 1991.
Takeshita et al., "Drug Action at a Cellular Level," Iryo, The Japanese Journal of the National Medical Services, Mar. 1979, vol. 33, No. 3, pp. 37-39.
Tanaka et al., "Cytotoxic Effects of Selenium on Mouse tsA640-transformed macrophages in vitro," Bulletin, Tottori University College of Medical Care Technology, 1992, No. 18, p. 13-20.
Viklicky et al., "SDZ-RAD Prevents Manifestation of Chronic Rejection in Rat Renal Allografts," Transplantation, 2000, vol. 69, No. 4, p. 497-502.
Funayama et al., "Plaque and Monocyte/Macrophage," Arteriosclerosis, 26(1): 37-40, 1998.
The Journal of the Japanese Society of Internal Medicine, 1997, vol. 86, No. 6, p. 883-888.
Diada et al., "Acute Coronary Syndrome-Diagnosis and Treatment," The Juntendo Medical Journal, Mar. 28, 2003, vol. 48, No. 4, pp. 448-457.

* cited by examiner

Control    LA 3 mg/kg

FIG. 3

METHOD OF TREATING ACUTE MYOCARDIAL INFARCTION

BACKGROUND OF THE INVENTION

Despite the advance in various therapeutic means, acute myocardial infarction (AMI) is still the leading cause of mortality in the western world. Acute myocardial infarction refers to a common clinical condition that leads to necrosis of myocardial tissue. This condition is well known in the art and is characterized by the occurrence of pain, in most cases precordial, characteristic electrocardiographic changes and an increase in plasma levels of intracellular enzymes released by the necrotic cardiac tissue such as creatinine phosphokinase and α-hydroxybutyrate dehydrogenase. AMI may be accompanied by hypotension, circulatory failure, pulmonary edema and arrhythmia. In most cases, but not exclusively, AMI results from vascular injury and thrombosis in the coronary vessels, which causes these vessels to become occluded with subsequent impaired blood flow to the jeopardized myocardium (Fuster, V. et al., 1992, New Engl. J. Med., 326:242 and 310). In most cases, the time of the occlusion of the coronary vessel can be estimated from the medical history, the course of plasma levels of intracellular heart muscle enzymes and electrocardiographic changes.

The initiating event of many myocardial infarctions (heart attacks) is rupture of an atherosclerotic plaque. Such rupture may result in formation of a thrombus or blood clot in the coronary artery which supplies the infarct zone. The infarct zone or area, as it is commonly referred to, is an area of necrosis which results from an obstruction of blood circulation. The thrombus formed is composed of a combination of fibrin and blood platelets. The formation of a fibrin-platelet clot has serious clinical ramifications. The location, degree and duration of the occlusion caused by the fibrin-platelet clot determine the mass of the infarct zone and the extent of damage.

Myocardial infarction occurs generally with an abrupt decrease in coronary blood flow to the infarct zone that follows a thrombotic occlusion of a coronary artery. The occluded artery often has been narrowed previously by atherosclerosis, and the risk of recurrent myocardial infarction persists in many patients. Ultimately, the extent of myocardial damage caused by the coronary occlusion depends upon the "territory" supplied by the affected vessel, the degree of occlusion of the vessel, the amount of blood supplied by collateral vessels to the affected tissue, and the demand for oxygen of the myocardium whose blood supply has suddenly been limited (Pasternak, R. and Braunwald, E., 1994, Acute Myocardial Infarction, Harrison's Principles of Internal Medicine, 13th Ed., pgs. 1066-77.)

Inflammation has been related both to the pathogenesis of acute myocardial infarctions and to the healing and repair following AMI. Myocardial ischemia prompts an inflammatory response. In addition, reperfusion, the mainstay of current acute therapy of AMI, also enhances inflammation. Reperfusion involves the rapid dissolution of the occluding thrombus and the restoration of blood flow to the area of the heart which has had its blood supply cut off. The presence of inflammatory cells in the ischemic myocardial tissues has traditionally been believed to represent the pathophysiological response to injury. However, experimental studies have shown that while crucial to healing, the influx of inflammatory cells into tissues, specifically macrophages which are phagocytic cells, results in tissue injury beyond that caused by ischemia alone.

Macrophages and other leukocytes infiltrate the myocardium soon after ischemia ensues. Macrophages secrete several cytokines, which stimulate fibroblast proliferation. However, the activated macrophages also secrete cytokines and other mediators that promote myocardial damage. Accordingly, the influx of macrophages into the myocardium increases myocardial necrosis and expands the zone of infarct. Thus, although the acute phase of inflammation is a necessary response for the healing process, persistent activation is in fact harmful to the infarct area as well as the area surrounding it, the so-called 'peri-infarct zone'.

The inflammatory response that follows myocardial ischemia is critical in determining the severity of the resultant damage caused by the activated macrophages. Plasma levels of inflammatory chemotactic factors (macrophage chemoattractant protein-1 (MCP-1), macrophage inflammatory protein-1 alpha (MIP-1 alpha), have been shown to correlate with subsequent heart failure and left ventricular dysfunction (See, for example, Parissis, J. T. et al., 2002, J. Interferon Cytokine Res., 22(2):223-9). Peripheral monocytosis (an elevated number of monocytes) at two and three days after AMI is associated with left ventricular dysfunction and left ventricular aneurysm, suggesting a possible role of monocytes in the development of left ventricular remodeling after reperfused AMI (Maekawa, Y. et al., 2002, J. Am. Coll. Cardiol., 39(2):241-6). Left ventricular remodeling after acute myocardial infarction is the process of infarct expansions followed by progressive left ventricular dilation and is associated with an adverse clinical outcome. Furthermore, plasma levels of macrophage chemoattractant protein-1 (MCP-1) are elevated in patients with acute myocardial infarction. MCP-1 is induced by myocardial ischemia/reperfusion injury and neutralization of this chemokine significantly reduced infarct size.

Suppression of the inflammatory response by nonspecific anti-inflammatory composites after coronary occlusion, in several coronary occlusion/reperfusion models, was shown to reduce the infarct area (See, for example, Squadrito, F. et al., 1997, Eur. J. Pharmacol.; 335:185-92; Libby, P. et al., 1973, J. Clin. Invest., 3:599-607; Spath J. A. et al., 1974, Circ. Res., 35: 44-51). However, these nonspecific regimens are associated with adverse effects, such as interference with scar formation and healing; and, leading in some patients, to the development of aneurysm and rupture of the ventricular wall. As such, these regimens are precluded from clinical use. On the other hand, animals deficient in the anti-inflammatory cytokine interleukin-10, that suppress macrophage function, were shown to suffer from increased infarct size and myocardial necrosis in a coronary occlusion model (Yang, Z. et al., 2000, Circulation, 101:1019-1026.)

A major therapeutic goal of modern cardiology is to design strategies aimed at minimizing myocardial necrosis and optimizing cardiac repair following myocardial infarction. One object of the invention is to describe methods which minimize the deleterious effects produced by an abrupt decrease in myocardial blood flow. It is another object of the invention to describe treatments that limit damage to the myocardium and the infarct area following acute myocardial infarction.

SUMMARY OF THE INVENTION

In accordance with the present invention, a method is provided to treat acute myocardial infarction. More particularly, the present invention relates to a method of minimizing myocardial necrosis, reducing the final zone of infarct and improving cardiac repair and outcome following acute myocardial infarction.

The present invention relates to a method of treating myocardial infarction by administering to an individual an effective amount of a formulation which inhibits and/or depletes phagocytic cells with high specificity, thereby suppressing the inflammatory response that occurs during and following acute myocardial infarction. The formulation comprises an agent which is an intra-cellular inhibitor that is released within the targeted phagocytic cells, specifically macrophages/monocytes, and inhibits and/or destroys the macrophages and/or monocytes, thereby reducing the final zone of infarct and improving cardiac repair and myocardial remodeling. Since macrophages and monocytes possess the unique ability to phagocytose large bodies, the agent is formulated into a specific size so that it can enter cells via phagocytosis. Thus, the specifically sized formulation selectively targets monocytes/macrophages. The formulation may comprise an encapsulated agent, an embedded agent or a particulate agent, wherein the formulation is of a specific size, such that it can primarily enter cells via phagocytosis.

In one embodiment, the present invention relates to a method of treating myocardial infarction by administering to an individual an effective amount of a formulation comprising an encapsulated agent. The agent is encapsulated in a suitable carrier of a specific dimension. The formulation specifically targets phagocytic cells by virtue of its properties, such as, for example, size, which allow the formulation to be taken-up primarily by phagocytosis. Once the formulation is taken-up by the phagocytic cells, the encapsulated agent is released and the agent is able to inhibit the activity of and/or destroy the phagocytic cells.

In a further embodiment, the present invention relates to a method of treating acute myocardial infarction by administering to an individual an effective amount of a formulation comprising an embedded agent. The agent is embedded in a suitable carrier of a specific dimension. The formulation specifically targets phagocytic cells by virtue of its properties, such as, for example, size, which allow the formulation to be taken-up primarily by phagocytosis. Once inside the phagocytic cells the embedded agent is released and the agent acts intra-cellularly to inactive and/or destroy the cells.

The present invention also relates to a method of treating acute myocardial infarction and reducing the zone of infarct by administering to an individual an effective amount of a formulation comprising a particulate agent. The formulation specifically targets phagocytic cells by virtue of its properties, such as, for example, size, which allow the formulation to be taken-up primarily by phagocytosis. Once inside the phagocytic cells the agent acts intra-cellularly to inactive and/or destroy the cells.

In a further embodiment, the present invention includes a pharmaceutical composition comprising a formulation selected from the group consisting of an encapsulated agent, an embedded agent, and a particulate agent together with a pharmaceutically acceptable carrier, stabilizer or diluent for the treatment of myocardial infarction.

The formulation of present invention is preferably in the size range of 0.03-1.0 microns. However, depending on the type of agent and/or the carrier used, the more preferred ranges include, but are not limited to, 0.1-0.5 microns, 0.1-0.3 microns and 0.1 to 0.18

DETAILED DESCRIPTION OF THE INVENTION

The present invention relates to formulations and methods for treating myocardial infarction. More particularly, the present invention includes a method of treating myocardial infarction by administering to an individual, an effective amount of an agent known to deplete, inactivate or inhibit blood monocytes and tissue macrophages. The agent is formulated such that it can primarily enter a cell via phagocytosis. For example, the agent may be encapsulated in a liposome of a specific size, embedded in a nanoparticle of a specific size, or formulated into particulate form, such as, for example, in aggregates of a specific size. The agent, when formulated into a particular size, specifically targets and is efficiently engulfed by way of phagocytosis by the macrophages and monocytes. Accordingly, the formulation does not target and thus does not affect non-phagocytic cells. Once inside the macrophages and/or monocytes, the agent is released and inactivates or destroys the cells. Depletion and/or inhibition of blood monocytes and tissue macrophages suppresses the inflammatory response following acute myocardial infarction. As a result, the final zone of infarct is reduced and myocardial remodeling is improved. Reduced infarct zone and proper remodeling correlates with decreased left ventricular dysfunction, decreased morbidity and decreased mortality.

The present invention encompasses an agent which is formulated so that it can primarily enter a cell via phagocytosis and selectively target macrophage and monocytes without affecting other non-phagocytic cells. Once inside the phagocytic cells, the agent is released and inhibits and/or depletes the monocytes and/or macrophages for treatment of myocardial infarction, reduction in the final zone of infarct and improvement of cardiac repair and outcome following acute myocardial infarction. The formulations may comprise an encapsulated agent, an embedded agent, or an agent in particulate form, all of a specific dimension, which allows up-take primarily via phagocytosis.

In one embodiment, the formulation comprises the agent encapsulated in a carrier of a specific size, hereinafter referred to as an "encapsulated agent." The term "encapsulated agent" includes an agent which is encapsulated within a carrier such as, for example, a liposome.

In a further embodiment, the formulation comprises the agent embedded in a carrier of a specific size hereinafter referred to an "embedded agent." The term "embedded agent" includes an agent which is embedded, enclosed, and/or adsorbed within a carrier, dispersed in the carrier matrix, adsorbed or linked on the carrier surface, or in combination of any of these forms. The carrier includes many forms, such as, for example, microparticles, nanoparticles, nanospheres, microspheres, microcapsules, or nanocapsules (e.g., M. Donbrow in: Microencapsulation and Nanoparticles in Medicine and Pharmacy, CRC Press, Boca Raton, Fla., 347, 1991). The term carrier includes both polymeric and non-polymeric preparations. In addition, suspending compounds and stabilizers may also be used with the encapsulated and/or embedded agent formulations.

In a further embodiment, the formulation comprises an agent in particulate form, hereinafter referred to as a "particulate agent." A "particulate agent" dosage form includes any insoluble suspended or dispersed particulate form of the agent of a specific dimension which is not encapsulated, entrapped or adsorbed within a carrier. Particulate agent formulations includes, but are not limited to, suspended or dispersed colloids, aggregates, flocculates, insoluble salts, insoluble complexes, and polymeric chains of an agent. Such particulates may also be aggregates of the polymerized agent. Typically, "insoluble" refers to a solubility of one (1) part of an agent in more than ten-thousand (10,000) parts of a solvent; the solvent, in this case, being blood (water). In addition, suspending agents and stabilizers may be used with the particulate agent formulation.

The formulation of the present invention, for example, the encapsulated agent, embedded agent or the particulate agent, suppresses the inflammatory response by transiently depleting and/or inactivating cells that are important triggers in the inflammatory response, namely macrophages and/or monocytes. The encapsulated agent, embedded agent and/or the particulate agent are taken-up, by way of phagocytosis, very efficiently by the macrophages and monocytes, and to some extent by other cells with phagocytic activity such as fibroblasts. In contrast, non-phagocytic cells are incapable of taking up the formulation due to the large dimension and/or other physiochemical properties of the formulation.

Once inside the macrophages, the structure of the encapsulated, embedded or particulate agent (e.g., liposome, microparticle, nanoparticle, aggregates) is disrupted and the agent is released intra-cellularly, thereby inhibiting the activity of, disabling and/or killing the monocytes/macrophages. Since macrophages and monocytes, in their normal state, are recruited to the infarcted area and promote myocardial damage beyond that caused by ischemia alone, monocyte/macrophage inhibition and/or depletion attenuates the myocardial damage. After being taken-up by the monocytes/macrophages, the agent has a sustained inhibitory activity on the monocytes/macrophages. This sustained activity is sufficient to modulate myocardial damage. Thus, prolonged release of the agent is not required in order to sustain inhibition. Accordingly, the method of treating myocardial infarction by inhibiting monocytes/macrophages, such as, for example, by the use of an encapsulated agent, an embedded agent or a particulate agent, is preferably a systemic therapy, in that the formulation targets the circulating monocytes and macrophages.

Furthermore, the formulation of the present invention not only retains the agent for a sufficient time so that the agent is not released in the body fluids, but also efficiently discharges the drug within the target cell. The agent is formulated into an encapsulated/embedded agent or a particulate agent because, in many instances, the agent in its free form is ineffective since it does not specifically target phagocytic cells. Encapsulating/embedding the agent in carrier particles of a specific size or formulating the agent into particulates, e.g. aggregates, of a specific size allows the formulations to be taken-up primarily and efficiently by macrophages and monocytes through phagocytosis.

The formulation, comprising an encapsulated agent, embedded agent or a particulate agent, is specifically sized so as to be taken-up by the macrophage and monocytes. The encapsulated, embedded, or particulate agent is preferably in the size range of 0.03-1.0 microns. However, depending on the type of agent and/or the carrier used, the more preferred ranges include, but are not limited to, 0.1-0.5 microns, 0.1-0.3 microns and 0.1 to 0.18 microns. These ranges, however, are merely examples and other size ranges suitable for up-take via phagocytosis will be recognized in the art and may be used without departing from the spirit or scope of the invention.

The agent includes any substance that once released within the targeted macrophages/monocytes inhibits and/or destroys the macrophages and monocytes to minimize myocardial necrosis and reduce the infarcted area. In accordance with the present invention, the agent comprises an intracellular inhibitor, deactivator, toxin, arresting substance and/or cytostatic/cytotoxic substance. That is, the agent includes any compound that once released within the targeted macrophages/monocytes inhibits, destroys, arrests, modifies and/or alters the macrophages and monocytes. The agent includes not only monomer, but also polymeric chains of the agent. One preferred class of agents are bisphosphonates. Free bisphosphonates, due to their affinity to bone and due to their inability to cross cellular membranes, have virtually no effect on the systemic inflammatory response. In contrast, bisphosphonates, when encapsulated in liposomes of a specific size, embedded in microparticles or nanoparticles of specific dimensions or when in a particulate formulation, such as, for example, in aggregates of a specific size, are specifically targeted to, and efficiently taken-up by way of phagocytosis, by the macrophages and monocytes. In contrast, non-phagocytic cells are incapable of taking-up the encapsulated bisphosphonates, embedded bisphosphonates and particulate bisphosphonates.

While the following detailed description often relates to a preferred embodiment of the present invention, i.e., the use of an encapsulated bisphosphonate, specifically, liposomal alendronate, it will be understood by the skilled practitioner in the art that any intra-cellular inhibitor, deactivator, toxin, arresting agent or cytostatic/cytotoxic agent, which is formulated into a specific size such that it can primarily enter a cell via phagocytosis, that can effectively deplete and/or inactivate monocytes/macrophages to minimize myocardial necrosis and improve cardiac repair following acute myocardial infarction, can be employed without departing from the spirit or scope of the invention. For instance, gallium and gold are inactivators of monocytes and macrophages and can be used as the agent of the present invention to treat acute myocardial infarction. Other agents useful in the present invention include, but are not limited to, selenium, gadolinium, silica, mithramycin, paclitaxel, sirolimus, and everolimus. Any intra-cellular inhibitor may be formulated as an encapsulated/embedded agent or a particulate agent of a specific size. Moreover, a combination of two or more inhibitors may be formulated into one dosage form for an improved effect.

In accordance with the present invention, a preferred class of agents are bisphosphonates. Bisphosphonates (formerly called diphosphonates) are compounds characterized by two C—P bonds. If the two bonds are located on the same carbon atom (P—C—P) they are termed geminal bisphosphonates. The bisphosphonates are analogs of the endogenous inorganic pyrophosphate which is involved in the regulation of bone formation and resorption. The term bisphosphonates is generally used for geminal and non-geminal bisphosphonates. The bisphosphonates may at times form polymeric chains. Bisphosphonates act on bone because of their affinity for bone mineral and also because they are potent inhibitors of bone resorption and ectopic calcification. Bisphosphonates have been clinically used mainly as (a) antiosteolytic agents in patients with increased bone destruction, especially Paget's disease, tumor bone disease and osteoporosis; (b) skeletal markers for diagnostic purposes (linked to $^{99m}$Tc); (c) inhibitors of calcification in patients with ectopic calcification and ossification, and (d) antitartar agents added to toothpaste (Fleisch, H., 1997, in: Bisphosphonates in bone disease. Parthenon Publishing Group Inc., 184-186). Furthermore, being highly hydrophilic and negatively charged, bisphosphonates in their free form are almost entirely incapable of crossing cellular membranes.

The bisphosphonates, when encapsulated in liposomes or embedded in carrier particles of specific dimensions, or when in a particulate dosage form, such as, for example, in aggregates of a specific size, can be used for the treatment of myocardial infarction. The term bisphosphonate as used herein, denotes both geminal and non-geminal bisphosphonates. A preferred agent, a bisphosphonate, has the following formula (I):

(I)

wherein $R_1$ is H, OH or a halogen atom; and $R_2$ is halogen; linear or branched $C_1$-$C_{10}$ alkyl or $C_2$-$C_{10}$ alkenyl optionally substituted by heteroaryl or heterocyclyl $C_1$-$C_{10}$ alkylamino or $C_3$-$C_8$ cycloalkylamino where the amino may be a primary, secondary or tertiary; —NHY where Y is hydrogen, $C_3$-$C_8$ cycloalkyl, aryl or heteroaryl; or $R_2$ is —SZ where Z is chlorosubstituted phenyl or pyridinyl.

One example of a preferred agent is the bisphosphonate, alendronate, having the following formula (II):

(II)

Additional bisphosphonates having activities similar to that of alendronate are also preferred in accordance with the invention. Such bisphosphonates may be selected on the basis of their ability to mimic the biological activity of alendronate. This includes, for example: in vitro activity in inhibiting activity of phagocytic cells, e.g. macrophages and fibroblasts; inhibition of secretion of IL-1 and/or IL-6 and/or TNF-α from macrophages; and in vivo activity, e.g. the ability of the tested formulations to deplete or disable blood monocytes in an animal model or in humans or to treat myocardial infarction and reduce the zone of infarct in an experimental animal model such as, for example, the rabbit acute myocardial infarction model described in Example 1 below.

Additional bisphosphonates applicable in the present invention, include, but are not limited to, clodronate, tiludronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3 (methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); and 1-hydroxy-2-(imidazo[1,2-a] pyridin-3-yl)ethane-1,1-diphosphonic acid, e.g. YM 529.

The term "effective amount" denotes an amount of the formulation which is effective in achieving the desired therapeutic result, namely treatment of myocardial infarction to minimize myocardial necrosis and improve cardiac repair. The decrease in number and activity of activated macrophages and monocytes reduces the zone of infarct and improves remodeling. The effective amount may depend on a number of factors including, but not limited to: weight and gender of the treated individual; the mode of administration of the formulation (namely whether it is administered systemically or directly to the site); the therapeutic regime (e.g. whether the formulation is administered once daily, several times a day, once every few days, or in a single dose); clinical indicators of inflammation; clinical factors influencing the rate of development of myocardial necrosis such as diabetes, smoking, hypercholesterolemia, pro-inflammatory states, renal diseases; and on the dosage form of the composition. The artisan, by routine experimentation, should have no substantial difficulties in determining the effective amount in each case.

The formulation used in accordance with the invention may be formulated into pharmaceutical compositions by any of the conventional techniques known in the art (see, for example, Alfonso, G. et al., 1995, in: *The Science and Practice of Pharmacy*, Mack Publishing, Easton Pa., 19th ed.). The formulations may be prepared in forms suitable for injection, instillation or implantation in the body, such as, for example, suspensions of the nanoparticles. In addition, the pharmaceutical compositions of the invention may be formulated with appropriate pharmaceutical additives for parenteral dosage forms. The preferred administration form in each case depends on the desired delivery mode, which is usually that which is the most physiologically compatible with the patient's condition and with the other therapeutic treatments which the patient currently receives.

The formulations may be administered by any route which effectively transports the formulation to the appropriate or desirable site of action. Preferred modes of administration include intravenous (IV) and intra-arterial (IA) (particularly suitable for on-line administration). Other suitable modes of administration include intramuscular (IM), subcutaneous (SC), and intraperitonal (IP). Such administration may be bolus injections or infusions. Another mode of administration may be by perivascular delivery. The formulation may be administered directly or after dilution. Combinations of any of the above routes of administration may also be used in accordance with the invention.

The dosage of the formulation to be used also depends on the specific activity of the agent selected, the mode of administration (e.g. systemic administration or local delivery), the form of the formulation (e.g. encapsulated agent, embedded agent, or particulate agent), the size of the formulation, and other factors as known per se. In one embodiment of the invention, the agent is encapsulated in liposomes. The liposomes may be prepared by any of the methods known in the art (regarding liposome preparation methods, see Mönkkönen, J. et al., 1994, *J. Drug Target*, 2:299-308, and Mönkkönen, J. et al., 1993, *Calcif. Tissue Int.*, 53:139-145). The liposomes may be positively charged, neutral or negatively charged, negatively charged liposomes being currently preferred, and may be single or multilamellar. Suitable liposomes in accordance with the invention are preferably non-toxic liposomes such as, for example, those prepared from phosphatidyl-choline phosphoglycerol, and cholesterol, e.g. as described below. The diameter of the liposomes used preferably range from 100 to 500 nm. However, other size ranges suitable for macrophage/monocyte up-take may also be used.

In a further embodiment, the agent may be embedded in nanoparticles. Nanoparticles are 30-1000 nm diameter, spherical or non-spherical polymeric particles. The agent may be embedded in the nanoparticle, dispersed uniformly or non-uniformly in the polymer matrix, adsorbed on the surface, or in combination of any of these forms. It is the submicron nature of this compositional form, which makes it efficient in therapeutic applications. The submicron size facilitates specific uptake by phagocytic cells such as monocytes and macrophages. In a preferred embodiment, the polymer used for fabricating nanoparticles is the biocompatible and biodegradable, poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyetheyleneglycols, polyethyleneoxides and their derivatives, chitosan, albumin, gelatin and the like. The size of the nanoparticle used to encapsulate the agent depends on the method of preparation and the mode of administration. Preferably, the nanoparticles range in size from 70-500 nm. However, depending on preparation and sterilization techniques, the more preferred ranges include, but are not limited to, 100-300 nm and 100-180 nm.

The pharmaceutical carrier or diluent used in the formulation of the invention may be any one of the conventional solid or liquid or semi-solid carriers known in the art. A solid carrier, for example, may be lactose, sucrose, gelatins, and other carbohydrates. A liquid carrier, for example, may be biocompatible oil suitable for injection such as peanut oil, water or mixtures of biocompatible liquids, or a biocompatible viscous carrier such as a polyethylene or gelatin gel.

The composition of the formulation used for injection may be selected from emulsions, suspensions, colloidal solutions containing suitable additives, and additional suitable compositions known to the skilled artisan.

In accordance with a preferred embodiment of the invention, the formulation is administered during an acute myocardial infarction or as early as possible after acute myocardial infarction occurs. However, for preventive purposes, the formulation may be administered prior to the onset of a myocardial infarction to those individuals who are at a high risk of a myocardial infarction. In addition, the formulation may also be administered prior to or after reperfusion to significantly attenuate myocardial injury. The formulation may also be administered prior to or during a procedure where an acute myocardial infarction is probable. For example, the formulation may be administered prior to a percutaneous transluminal coronary angioplasty (PTCA). In addition, the formulation may be administered to the individual either alone or in combination with other kinds of treatments.

In a further embodiment, the formulation may be administered to patients at risk of an impending myocardial infarction, to those with unstable coronary syndromes, or to those with myocardial ischemia.

In conclusion, modulation of the inflammatory response by specifically targeting monocytes and macrophages may reduce necrosis and improve cardiac repair and function after acute myocardial infarction.

EXAMPLE(S)

The following examples as set forth herein are meant to illustrate and exemplify the various aspects of carrying out the present invention and are not intended to limit the invention in any way.

Example 1: Effect of Liposomal Alendronate on the Zone of Infarct

The effects of treatment with encapsulated bisphosphonates on the zone of infarct were studied in a rabbit AMI model. Eight New Zealand White male rabbits, 2.5-3.5 kg B.W., were fed normal chow and water ad libitum. The rabbits were anesthetized by Ketamine/Xylazine (35 mg/kg; 5 mg/kg) and Isoflurane. The experiment was performed with respiratory support given by intubation and mechanical ventilation with isoflurane in balance oxygen, and continuous echocardiogram (ECG) and arterial blood pressure (catheter in ear artery) monitoring. The rabbits were randomly administered saline (control) or liposomal alendronate (3 mg/kg, i.v.). Thoracotomy was performed through the left $4^{th}$ intercostal space, followed by pericardiotomy and creation of a pericardial cradle. The left main coronary artery was identified and a large branch was encircled by a 5-0 silk suture and a snare. Thereafter, the snare was tightened for 30 minutes. Ischemia was verified by ECG changes (ST-T segment elevation), changes of segment coloration and hypokinesia. After thirty minutes, the snare was released and resumption of blood flow was confirmed. The suture was left in place, released, and the chest cavity was closed in layers. Buprenex was administered to the rabbits for analgesia for 2-3 additional days. Following euthanasia with Penthotal, the rabbits were sacrificed after 7 days and the hearts were harvested. The coronary arteries were perfused through the ascending aorta with saline, followed by tightening of the suture on the previously occluded coronary artery and perfusion of the coronary arteries with 0.5% Evans blue solution (Sigma). The hearts were then frozen at −20° C. for 24 hours and cut into transverse sections 2 mm apart. Slices of the hearts were incubated for 30 minutes in tritetrazolium chloride (TTC, 1%, Sigma), fixed in 10% natural buffered formalin, and then photographed and processed by digital planimetry (photoshop). The left ventricular area unstained by Evans blue was defined as the area at risk and the area not stained by TTC (white) was defined as the area of infarct.

Figure 1:
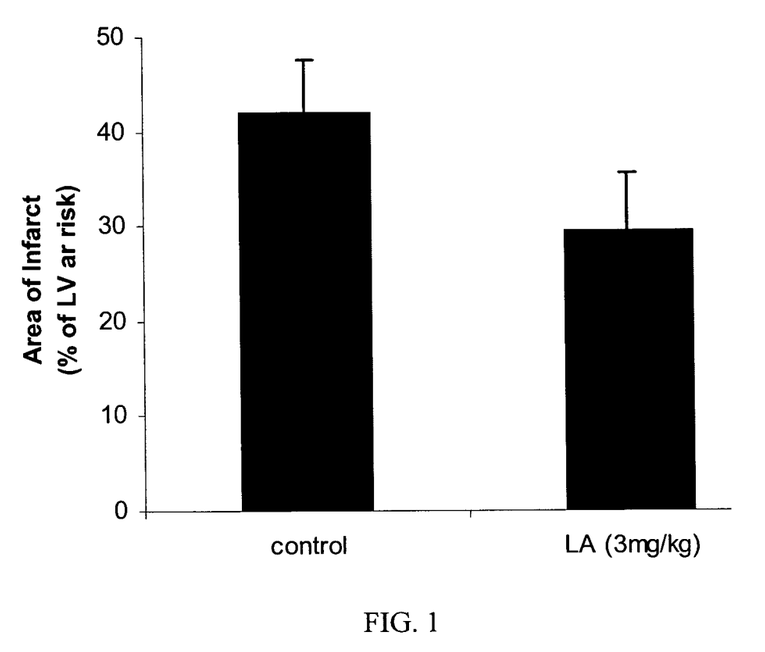
FIG. 1 illustrates the effect of liposomal alendronate treatment on the infarct area after transient coronary artery occlusion in rabbits. The results present the area of the infarcted zone as a % of the left ventricular area supplied by the occluded artery and at risk for subsequent infarction.

The results of liposomal alendronate on the final zone or area of infarct are shown in FIG. 1. The results are presented as percentage of infarcted zone out of the area at risk. As illustrated, the area or zone of infarct was 42±5.5% in the control group and 29.5±6% in the group treated with liposomal alendronate. The data in FIG. 1 are expressed as mean±SD, n=4/group, p<0.05. Accordingly, liposomal alendronate was effective in reducing the zone of infarct. No adverse effects were observed in the treatment group.

Figure 2:
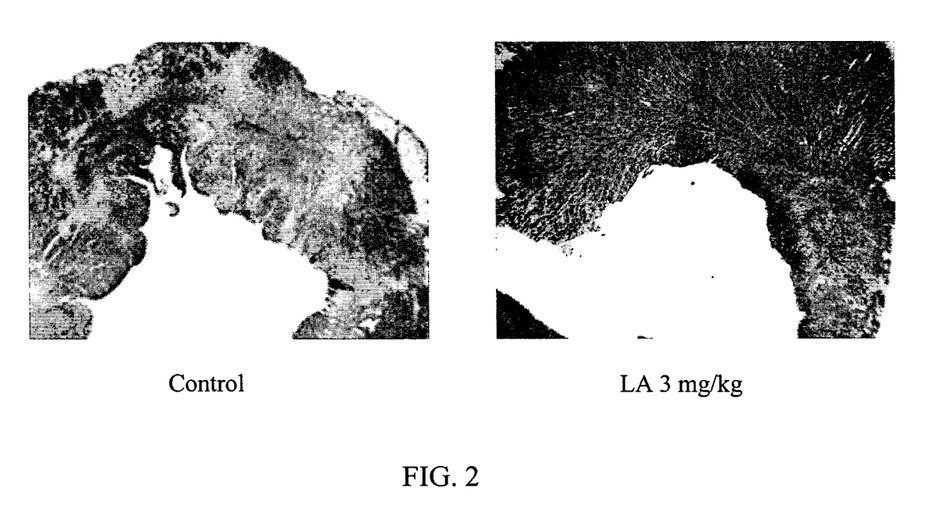
FIG. 2 illustrates the effect of liposomal alendronate treatment on myocardial morphometry after reversible coronary occlusion in rabbits.

The variation in myocardial morphometry is illustrated in FIG. 2. The control rabbits have a distorted myocardial morphometry while the rabbits treated with liposomal alendronate exhibit a more normal morphometry.

In addition, the effect of liposomal alendronate on blood monocytes was also determined. Monocyte suppression was ascertained using FACS analysis. At 48 hours after injection with liposomal alendronate, the blood monocyte population was reduced by 75-95%.

Figure 3:
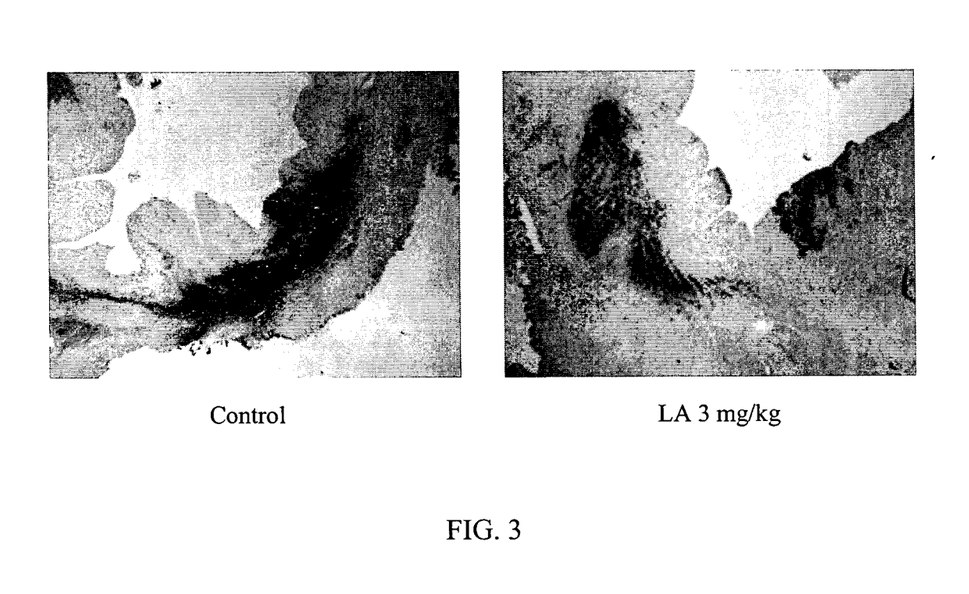
FIG. 3 illustrates the reduction in macrophage infiltration following treatment with liposomal alendronate after reversible coronary occlusion in rabbits.

Similarly, FIG. 3 illustrates the reduction in macrophage infiltration in rabbits treated with liposomal alendronate. The reduction in macrophage infiltration was ascertained by immunostaining for RAM11+ macrophages in representative sections of rabbit's hearts from the control group and those treated with liposomal alendronate.

The contents of all published articles, books, reference manuals, and abstracts as cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

The invention claimed is:

1. A method of treating a patient experiencing an acute myocardial infarction comprising:
    in response to onset of said acute myocardial infarction, administering an effective amount of a formulation to said patient in need thereof, said formulation comprising a bisphosphonate encapsulated in a particle, embedded in a particle, or in a particulate, said particle or particulate having a size from 0.03 to 1.0 micron;
    wherein the formulation inhibits blood monocytes or tissue macrophages by decreasing cell activity or cell numbers of the blood monocytes or tissue macrophages; and
    wherein the inhibiting of the blood monocytes or tissue macrophages, reduces a myocardial zone of infarct of said patient resulting from said acute myocardial infarction.

2. The method as in claim 1, wherein the formulation has a size range of 0.07 to 0.5 microns.

3. The method as in claim 1, wherein the formulation has a size range of 0.1 to 0.5 microns.

4. The method as in claim 1, wherein the formulation has a size range of 0.1 to 0.3 microns.

5. The method as in claim 1, wherein the formulation has a size range of 0.1 to 0.18 microns.

6. The method as in claim 1, wherein the bisphosphonate is an intra-cellular inhibitor.

7. The method as in claim 1, wherein the formulation can primarily enter a cell via phagocytosis.

8. The method according to claim 1, wherein the bisphosphonate is selected from the group consisting of clodronate, etidronate, tiludronate, pamidronate, alendronate and risendronate.

9. The method according to claim 1, wherein the bisphosphonate is encapsulated in a liposome.

10. The method according to claim 1, wherein inhibition of said monocytes or macrophages occurs through phagocytosis of the formulation.

11. The method according to claim 1, wherein said bisphosphonate has formula (I):

wherein $R_1$ is H, OH or halogen group; and
$R_2$ is halogen; linear or branched $C_1$-$C_{10}$ alkyl or $C_2$-$C_{10}$ alkenyl, optionally substituted by heteroaryl or heterocyclyl $C_1$-$C_{10}$ alkylamino or $C_3$-$C_8$ cycloalkylamino, where the amino may be a primary, secondary or tertiary amine; —NHY where Y is hydrogen, $C_3$-$C_8$ cycloalkyl, aryl or heteroaryl; or —SZ, where Z is chlorosubstituted phenyl or pyridinyl.

* * * * *